(12) United States Patent
Nelson et al.

(10) Patent No.: US 10,076,387 B2
(45) Date of Patent: Sep. 18, 2018

(54) MEDICAL DEVICE IMPLANTATION AND POSITIONING SYSTEM

(71) Applicant: Medtronic, Inc., Minneapolis, MN (US)

(72) Inventors: Brian D. Nelson, Birchwood, MN (US); Jason E. Agran, Coon Rapids, MN (US)

(73) Assignee: MEDTRONIC, INC., Minneapolis, MN (US)

(*) Notice: Subject to any disclaimer, the term of this patent is extended or adjusted under 35 U.S.C. 154(b) by 310 days.

(21) Appl. No.: 14/947,044

(22) Filed: Nov. 20, 2015

(65) Prior Publication Data
US 2016/0367331 A1 Dec. 22, 2016

Related U.S. Application Data

(60) Provisional application No. 62/181,373, filed on Jun. 18, 2015.

(51) Int. Cl.
*A61B 90/11* (2016.01)
*A61B 90/10* (2016.01)
(Continued)

(52) U.S. Cl.
CPC .......... *A61B 90/11* (2016.02); *A61B 17/3468* (2013.01); *A61B 90/10* (2016.02); *A61B 2017/3407* (2013.01); *A61B 2017/3409* (2013.01); *A61B 2034/2055* (2016.02); *A61B 2090/363* (2016.02)

(58) Field of Classification Search
CPC ......... A61B 90/10; A61B 90/11; A61B 34/30; A61B 2090/103
See application file for complete search history.

(56) References Cited

U.S. PATENT DOCUMENTS 3,021,842 A   2/1962  Flood
3,262,452 A   7/1966  Hardy et al.
(Continued)

FOREIGN PATENT DOCUMENTS

DE   19726141 A1   1/1999
DE   19808220 A1   9/1999

OTHER PUBLICATIONS

"CRW Precision™ Arc stereotactic system." Brochure. Integra LifeSciences Corporation. Plainsboro, NJ, 2009; 12 pages.
(Continued)

*Primary Examiner* — Julie A Szpira
(74) *Attorney, Agent, or Firm* — Mueting, Raasch & Gebhardt, P.A.

(57) ABSTRACT

An implantation system for positioning and aligning an elongate medical device in three-dimensional space. The system may include: a frame member; and first, second, and third legs each having an adjustable length. Each of the first, second, and third legs includes: a first end having a socket segment, wherein the socket segments of each of the first, second, and third legs together define a socket; and a second end connected to the frame member. A spherical member is adapted to be received within the socket such that the spherical member may rotate about a center of rotation defined by the socket, the spherical member having an inner surface defining a bore passing through the spherical member.

17 Claims, 12 Drawing Sheets

(51) Int. Cl.
  *A61B 17/34* (2006.01)
  *A61B 90/00* (2016.01)
  *A61B 34/20* (2016.01)

(56) References Cited

U.S. PATENT DOCUMENTS

| | | |
|---|---|---|
| 3,444,861 A | 5/1969 | Schulte |
| 3,760,811 A | 9/1973 | Andrew |
| 3,822,697 A | 7/1974 | Komiya |
| 3,853,127 A | 12/1974 | Spademan |
| 4,025,964 A | 5/1977 | Owens |
| 4,243,034 A | 1/1981 | Brandt |
| 4,311,137 A | 1/1982 | Gerard |
| 4,328,813 A | 5/1982 | Ray |
| 4,350,159 A | 9/1982 | Gouda |
| 4,360,025 A | 11/1982 | Edwards |
| 4,449,527 A | 5/1984 | Hinton |
| 4,516,968 A | 5/1985 | Marshall et al. |
| 4,518,145 A | 5/1985 | Keltz et al. |
| 4,629,451 A | 12/1986 | Winters et al. |
| 4,681,103 A | 7/1987 | Boner et al. |
| 4,805,615 A | 2/1989 | Carol |
| 4,805,634 A | 2/1989 | Ulrich et al. |
| 4,993,425 A | 2/1991 | Kronberg |
| 5,030,205 A | 7/1991 | Holdaway et al. |
| 5,030,223 A | 7/1991 | Anderson et al. |
| 5,126,090 A | 6/1992 | Egolf et al. |
| 5,158,569 A | 10/1992 | Strickland et al. |
| 5,183,465 A | 2/1993 | Xanthakos et al. |
| 5,263,956 A | 11/1993 | Nobles |
| 5,368,573 A | 11/1994 | Andrew |
| 5,464,446 A | 11/1995 | Dreessen et al. |
| 5,540,648 A | 7/1996 | Yoon |
| 5,603,703 A | 2/1997 | Elsberry et al. |
| 5,662,600 A | 9/1997 | Watson et al. |
| 5,713,858 A | 2/1998 | Heruth et al. |
| 5,752,962 A | 5/1998 | D'Urso |
| 5,843,150 A | 12/1998 | Dreessen et al. |
| 5,865,842 A | 2/1999 | Knuth et al. |
| 5,916,200 A | 6/1999 | Eppley et al. |
| 5,927,277 A | 7/1999 | Baudino et al. |
| 5,954,687 A | 9/1999 | Baudino |
| 5,989,223 A | 11/1999 | Chu et al. |
| 6,044,304 A | 3/2000 | Baudino |
| 6,132,437 A | 10/2000 | Omurtag et al. |
| 6,134,477 A | 10/2000 | Knuteson |
| 6,210,417 B1 | 4/2001 | Baudino et al. |
| 6,321,104 B1 | 11/2001 | Gielen et al. |
| 6,328,748 B1 | 12/2001 | Hennig |
| 6,355,028 B2 | 3/2002 | Castaneda et al. |
| 6,356,792 B1 | 3/2002 | Errico et al. |
| 6,482,182 B1 | 11/2002 | Carroll et al. |
| 6,591,472 B1 | 7/2003 | Noone et al. |
| 6,609,020 B2 | 8/2003 | Gill |
| 6,902,569 B2 | 6/2005 | Parmer et al. |
| 7,004,948 B1 | 2/2006 | Pianca et al. |
| 7,204,840 B2 | 4/2007 | Skakoon et al. |
| 7,454,251 B2 | 11/2008 | Rezai et al. |
| 7,553,298 B2 | 6/2009 | Hunt et al. |
| 7,580,756 B2 | 8/2009 | Schulte et al. |
| 7,636,596 B2 | 12/2009 | Solar |
| 7,637,915 B2 | 12/2009 | Parmer et al. |
| 7,704,260 B2 | 4/2010 | Skakoon et al. |
| 7,730,628 B2 | 6/2010 | Hoffman |
| 7,794,469 B2 | 9/2010 | Kao et al. |
| 7,806,886 B2 | 10/2010 | Kanderian, Jr. et al. |
| 7,828,809 B2 | 11/2010 | Skakoon et al. |
| 7,879,045 B2 | 2/2011 | Gielen et al. |
| 7,981,119 B2 | 7/2011 | Lando et al. |
| 7,988,674 B2 | 8/2011 | Adams et al. |
| 8,075,531 B2 | 12/2011 | Davey |
| 8,603,038 B2 | 12/2013 | Nelson |
| 8,738,151 B2 | 5/2014 | Nelson |
| 9,113,949 B2 | 8/2015 | Nelson |
| 9,302,043 B2 | 4/2016 | Nelson |
| 2002/0019641 A1 | 2/2002 | Truwit |
| 2002/0042605 A1 | 4/2002 | Castaneda et al. |
| 2002/0052610 A1 | 5/2002 | Skakoon et al. |
| 2002/0151871 A1 | 10/2002 | Gaiser et al. |
| 2002/0169460 A1 | 11/2002 | Foster et al. |
| 2003/0040753 A1 | 2/2003 | Daum et al. |
| 2003/0114752 A1 | 6/2003 | Henderson et al. |
| 2003/0199831 A1 | 10/2003 | Morris et al. |
| 2004/0034367 A1 | 2/2004 | Malinowski |
| 2004/0243146 A1 | 12/2004 | Chesbrough et al. |
| 2004/0267284 A1 | 12/2004 | Parmer et al. |
| 2005/0054985 A1 | 3/2005 | Mogg |
| 2005/0125007 A1 | 6/2005 | Gill |
| 2005/0143799 A1 | 6/2005 | Black et al. |
| 2005/0143800 A1 | 6/2005 | Lando et al. |
| 2005/0182464 A1 | 8/2005 | Schulte et al. |
| 2005/0192594 A1 | 9/2005 | Skakoon et al. |
| 2005/0256455 A1 | 11/2005 | Weststrate et al. |
| 2006/0111688 A1 | 5/2006 | Krause et al. |
| 2006/0122628 A1 | 6/2006 | Solar et al. |
| 2006/0129126 A1 | 6/2006 | Kaplitt et al. |
| 2007/0066977 A1 | 3/2007 | Assell et al. |
| 2007/0106305 A1* | 5/2007 | Kao ............... A61B 90/11 606/130 |
| 2007/0149977 A1 | 6/2007 | Heavener |
| 2008/0161719 A1 | 7/2008 | Miller et al. |
| 2008/0200798 A1 | 8/2008 | Ecklund et al. |
| 2008/0275466 A1 | 11/2008 | Skakoon |
| 2009/0143764 A1 | 6/2009 | Nelson |
| 2009/0187149 A1 | 7/2009 | Nelson |
| 2009/0306501 A1 | 12/2009 | Flint |
| 2010/0030184 A1 | 2/2010 | Boulis et al. |
| 2010/0042111 A1* | 2/2010 | Qureshi ............. F16M 11/14 606/130 |
| 2010/0174240 A1 | 7/2010 | Wells et al. |
| 2010/0217196 A1 | 8/2010 | Nelson |
| 2010/0312280 A1 | 12/2010 | Overes et al. |
| 2011/0009879 A1 | 1/2011 | Derrick et al. |
| 2011/0040304 A1 | 2/2011 | Li et al. |
| 2011/0190789 A1 | 8/2011 | Thiran et al. |
| 2011/0270187 A1 | 11/2011 | Nelson |
| 2011/0295271 A1 | 12/2011 | Kao et al. |
| 2012/0083742 A1 | 4/2012 | Nelson |
| 2013/0072876 A1 | 3/2013 | Pretre et al. |
| 2013/0085342 A1* | 4/2013 | Stefanchik ......... A61B 17/3417 600/232 |
| 2013/0096570 A1 | 4/2013 | Solar et al. |
| 2014/0276416 A1 | 9/2014 | Nelson et al. |
| 2014/0276418 A1 | 9/2014 | Nelson et al. |
| 2014/0276529 A1 | 9/2014 | Bodner |

OTHER PUBLICATIONS

"Leksell Stereotactic System® overview." Brochure. Elekta AB, Stockholm, Sweden. Sep. 2010; 22 pages.
"MicroTargeting™ STar™ Drive System, Directions for Use." FHC, Inc., Bowdoin, ME. Oct. 2010; 49 pages.
"MicroTargeting™ STar™ Drive System, Directions for Use." FHC, Inc., Bowdoin, ME. Mar. 2013; 53 pages.
"STar™ Drive System." Datasheet. FHC, Inc., Bowdoin, ME. Sep. 2012; 2 pages.
"STarFix™ Platform System for Direct Targeting." Datasheet. FHC, Inc., Bowdoin, ME. Date unavailable; 2 pages.
U.S. Appl. No. 62/181,373, filed Jun. 18, 2015, Nelson et al.
"STarFix™ Platform." Datasheet. FHC, Inc., Bowdoin, ME. Jun. 2012; 2 pages.
"StealthStation® S7® System." Datasheet. Medtronic, Inc., Louisville, CO. 2013; 2 pages.
"StealthViz® with StealthDTI® Module." Datasheet. Medtronic, Inc., Louisville, CO. 2013; 4 pages.
"STIMLOC by ign." Datasheet. Image Guided Neurologics, Inc., Melbourne, FL. 2004; 2 pgs.
International Search Report and Written Opinion for International Application No. PCT/US2016/036675, dated Aug. 17, 2016; 13 pgs.

* cited by examiner

MEDICAL DEVICE IMPLANTATION AND POSITIONING SYSTEM

This application claims the benefit of U.S. Provisional Application No. 62/181,373, filed 18 Jun. 2015, which is incorporated herein by reference in its entirety.

Embodiments described herein are directed generally to device (e.g., medical device) placement, and, more particularly, to systems, apparatus, and methods for precision-guided alignment and implantation of a therapy delivery device (e.g., a catheter, electrode, or lead).

BACKGROUND

Medical procedures involving precision insertion and placement of a therapy delivery device into a patient through a body portal are used to treat a variety of medical conditions. For example, electrical deep brain stimulation (DBS) to relieve chronic pain, or for the treatment of movement disorders, may necessitate the implantation, via a burr hole formed in the skull, of an electrode or lead. Similarly, burr holes are typically formed to allow implantation of a therapy catheter, e.g., an intraparenchymal (IPA) or intracerebroventricular catheter, to treat various ailments.

Use of such devices to deliver therapy to the brain generally involves determining: a cranial entry point; a depth to the desired target tissue location; and a device trajectory. To then accurately place the therapy delivery device, surgeons typically use stereotactic apparatus/procedures.

Stereotactic apparatus of varying configurations are known. For example, a "center-of-arc" stereotactic apparatus includes an arc-shaped frame wherein a center of the frame, as well as a pivot about which the frame is movable, aligns with the target tissue location. As a result, multiple device trajectory and entry points are available to reach the target location. Other stereotactic systems may utilize what is referred to as "frameless" or "microframe" technology. These systems typically utilize a pre-aligned, stereotactic platform custom-made for a particular patient's cranial physiology. Such systems may allow pre-operative alignment and configuration (potentially reducing the patient's time in the operating room) and may further result in less discomfort to the patient. These systems are advantageous in that they may also easily accommodate bilateral implantations.

While providing accurate device placement, microframe systems may present drawbacks. For example, the custom-made platform presents a recurring fee for each patient as compared to re-usable platforms. Moreover, it may take days to receive the custom platform after an order is placed, reducing the opportunity to offer same-day planning and surgery. Still further, such custom-made systems may have little or no ability to accommodate subsequent targeting adjustments when needed (e.g., when a large blood vessel is later found within the planned implant trajectory).

SUMMARY

Stereotactic systems that may overcome these and other issues may be provided by apparatus, systems, and methods in accordance with embodiments of the present disclosure. For instance, embodiments described herein may provide an implantation system for positioning an elongate medical device in three-dimensional space. The system may include: a frame member; and first, second, and third legs each having an adjustable length. Each of the first, second, and third legs includes: a first end comprising a socket segment, wherein the socket segments of each of the first, second, and third legs together define a socket; and a second end connected to the frame member. A spherical member is also provided and adapted to be received within the socket such that the spherical member may rotate about a center of rotation defined by the socket. The spherical member includes an inner surface defining a bore passing through the spherical member.

In another embodiment, a system for implanting an elongate medical device into a mammalian skull through a predetermined entry point and at a predetermined trajectory is provided, wherein the system includes: a frame comprising three or more anchor points; and a spherical guide assembly. The spherical guide assembly may include: three independent socket segments that together define a socket; and a spherical member adapted to be received within the socket such that the spherical member may rotate about a center of rotation defined by the socket, wherein the spherical member includes an inner surface defining a bore passing through the spherical member. The system further includes first, second, and third legs, wherein each of the first, second, and third legs has an adjustable length, and wherein each of the first, second, and third legs is connected both to the spherical guide assembly and to the frame.

In yet another embodiment, a method for configuring an implantation system for an elongate medical device is provided, wherein the method includes: establishing a coordinate system based upon positions of three or more reference points on a surface of a body; and determining coordinates of a target tissue location within the body based upon the coordinate system. The method further includes positioning a center of rotation of a socket of a spherical guide assembly relative to the target tissue location to provide an implant trajectory. The spherical guide assembly includes: three independent socket segments that together define the socket; and a spherical member adapted to be received within the socket such that the spherical member may rotate about the center of rotation defined by the socket. The spherical member also includes an inner surface defining a bore passing through the spherical member. The method further includes supporting the spherical guide assembly with first, second, and third legs, wherein each of the first, second, and third legs has an adjustable length, and wherein each of the first, second, and third legs is connected both to the spherical guide assembly and to a ring adapted to connect to the three or more reference points. The method also includes: engaging a leg lock associated with each of the first, second, and third legs when the center of rotation aligns with the implant trajectory; and adjusting a rotational position of the spherical member within the socket until an axis of the bore of the spherical member is coincident with the implant trajectory.

The above summary is not intended to describe each embodiment or every implementation. Rather, a more complete understanding of illustrative embodiments will become apparent and appreciated by reference to the following Detailed Description of Exemplary Embodiments and claims in view of the accompanying Figures of the drawing.

BRIEF DESCRIPTION OF THE VIEWS OF THE DRAWING

Exemplary embodiments will be further described with reference to the Figures of the drawing, wherein:

FIGS. 9A and 9B illustrate exemplary positioning and alignment systems in accordance with embodiments of the present disclosure, wherein: FIG. 9A illustrates a system utilizing a coordinate measuring machine (CMM); and FIG. 9B illustrates a system utilizing an optical measuring apparatus;

Figure 1:
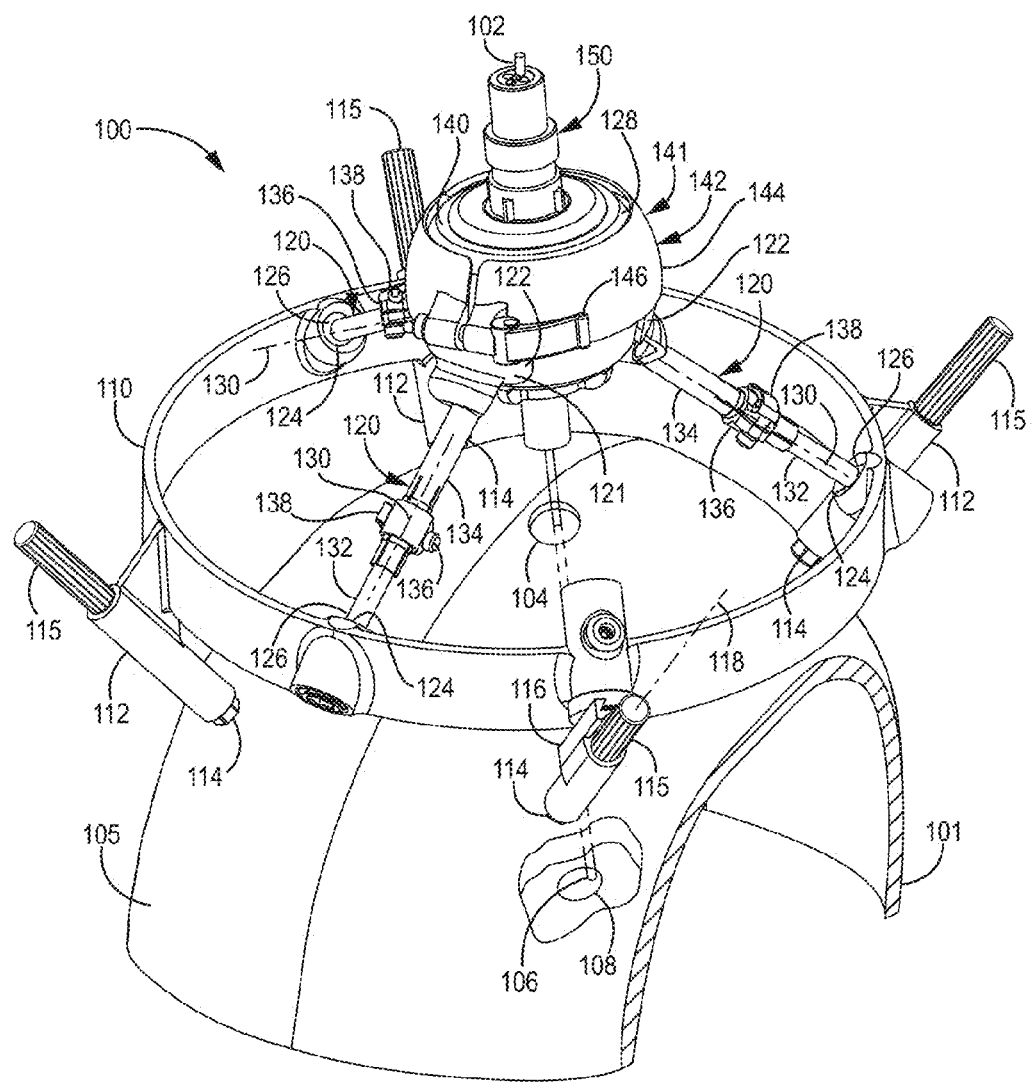
FIG. 1 is a perspective view of a unilateral implantation system (e.g., having a single spherical guide assembly) in accordance with one embodiment of the disclosure, the system adapted to position an elongate medical device in three-dimensional space (e.g., within a cranial cavity or other portion of a mammalian body)

The Figures are rendered primarily for clarity and, as a result, are not necessarily drawn to scale. Moreover, various structure/components, including but not limited to fasteners, electrical components (wiring, cables, etc.), and the like, may be shown diagrammatically or removed from some or all of the views to better illustrate aspects of the depicted embodiments, or where inclusion of such structure/components is not necessary to an understanding of the various exemplary embodiments described herein. The lack of illustration/description of such structure/components in a particular figure is, however, not to be interpreted as limiting the scope of the various embodiments in any way. Still further, "Figure x" and "FIG. x" may be used interchangeably herein to refer to the Figure numbered "x."

DETAILED DESCRIPTION OF EXEMPLARY EMBODIMENTS

In the following detailed description of illustrative embodiments, reference is made to the accompanying figures of the drawing which form a part hereof. It is to be understood that other embodiments, which may not be described and/or illustrated herein, are certainly contemplated.

All headings provided herein are for the convenience of the reader and should not be used to limit the meaning of any text that follows the heading, unless so specified. Moreover, unless otherwise indicated, all numbers expressing quantities, and all terms expressing direction/orientation (e.g., vertical, horizontal, parallel, perpendicular, etc.) in the specification and claims are to be understood as being modified in all instances by the term "about."

In general, embodiments of the present disclosure include systems, apparatus, and methods for positioning an elongate device in three-dimensional space (e.g., implantation systems for positioning an elongate medical device within a mammalian body). Such systems may include: a frame member; and first, second, and third legs each having an adjustable length. Each of the first, second, and third legs may include: a first end forming (or otherwise connecting to) a socket segment, wherein the socket segments of each of the first, second, and third legs together define a socket; and a second end connected to the frame member. A spherical member may also be included and adapted to be received within the socket such that the spherical member may rotate about a center of rotation defined by the socket. The spherical member may include an inner surface defining a bore adapted to receive and secure an insertion guide such as a center positioner, cannula, surgical insertion drive, etc.

By first indexing the frame member relative to a body (e.g., skull) surface, adjustments to both the leg length and to the rotational position of the spherical member may be pre-operatively determined and then set or "locked" relative to the frame member. The surgeon may then transfer the pre-configured system directly to the patient, whereby the system maintains the pre-operatively (predetermined) body entry point and device trajectory without requiring further intra-operative system adjustment. While implantation systems in accordance with embodiments of the present disclosure may permit pre-operative configuration of the system, they may also allow subsequent intra-operative adjustments when such adjustments are deemed necessary or beneficial. Still further, some of the recurring costs associated with known systems utilizing customized frames may be reduced or, potentially, even eliminated.

It is noted that the term "comprises" and variations thereof do not have a limiting meaning where these terms appear in the accompanying description and claims. Further, "a," "an," "the," "at least one," and "one or more" are used interchangeably herein. Moreover, relative terms such as "left," "right," "front," "fore," "forward," "rear," "aft," "rearward," "top," "bottom," "side," "upper," "lower," "above," "below," "horizontal," "vertical," and the like may be used herein and, if so, are from the perspective observed in the particular figure. These terms are used only to simplify the description, however, and not to limit the interpretation of any embodiment described.

With reference to the figures of the drawing, wherein like reference numerals designate like parts and assemblies throughout the several views, FIG. 1 illustrates an exemplary apparatus for positioning an elongate element or device in three-dimensional space. In some embodiments, such an apparatus may be configured as an implantation system 100 adapted to implant an elongate medical device 102 (e.g., a lead (e.g., DBS lead) or catheter) into a mammalian body 101. For example, the system may be designed to accurately position the lead (or catheter), through a body portal (e.g., through a burr hole 104 formed in a human (or other mammalian) skull 105), and locate a therapy delivery tip 106 of the lead or catheter at a desired target tissue location 108. While illustrated as a burr hole accommodating device implantation into brain tissue, such a configuration is not limiting. Rather, systems like those described herein may be used to implant a medical device at most any anatomical location (e.g., intra-spinal).

In the embodiment shown in FIG. 1, the implantation system 100 may include a frame or frame member 110 adapted to secure to the body 101 (e.g., skull 105) using three or more anchor points 112. While not wishing to be bound to any exact geometry, the frame member 110 may, in some embodiments, form a ring, e.g., generally circular ring, as shown in FIG. 1 (however, other non-circular ring shapes (e.g., obround, elliptical, oval, triangle, or other polygon) are certainly possible).

Each of the anchor points 112 may be used to secure the ring/frame member 110 to a corresponding reference point on the patient's body 101 (e.g., skull 105). The reference points may, in some embodiments, be formed by fiducials 114 (e.g., metallic fiducials) that have been previously attached to the skull 105 as further described below. For example, thumb screws 115 may pass through the anchor points 112 and thread into the respective fiducials 114 as shown in FIG. 1 and further described below.

While three anchor points 112 are sufficient to define a plane of attachment, some embodiments may include additional anchor points and corresponding fiducials. For instance, in the illustrated embodiment, a supplemental anchor point 116 may be included and configured to attach to a corresponding fiducial 114. The three primary anchor points 112 may be fixed to the frame member and thus may be sufficient to statically secure the frame member 110 relative to the skull 105. However, the supplemental anchor point 116 may be configured as a sliding anchor point in that it initially slides (e.g., along an axis 118) relative to the frame member 110. Accordingly, once the primary anchors 112 are secured to their corresponding fiducials 114, the anchor point 116 may be slid toward the skull surface and into contact with its associated fiducial. The anchor point 116 may then be locked in place (relative to the frame member 110), e.g., using a locking fastener (not shown), thereby providing the system 100 with four rigid anchor points.

The system 100 may also include three (e.g., first, second, and third) legs 120 each having an adjustable length, wherein each of the first, second, and third legs may in some embodiments, be generally identical to the others. Each of the legs 120 may have a first end 121 attached to (e.g., forming) a socket segment 122, wherein the socket segments 122 of all three legs together define a socket 128 as described in more detail below. In the illustrated embodiments, each socket segment 122 is formed by an integral, concave end portion of the respective leg 120 as shown, for example, in FIG. 6. A second end 126 of each of the legs 120 may form a ball (see, e.g., FIGS. 4 and 5) received within a leg socket 124 formed in the frame member 110. Accordingly, each of the legs 120 may pivot about its respective second end 126/leg socket 124 relative to the frame member 110. Due to this ball-and-socket connection, each of the legs 120 may also rotate about its respective longitudinal axis 130. In other embodiments where rotational freedom of one or more of the legs 120 about their respective axes 130 is not needed or desired, the ball-and-socket connection may be replaced with another connection type, e.g., a U-joint or the like.

As shown in FIG. 1 (and further described below), each of the legs 120 may also be adjustable in length (e.g., along the axis 130). In some embodiments, this is accomplished by providing a first leg element 132 that is telescopingly received within a second leg element 134. One or both of the mating ends of first and second leg elements 132, 134 may be slit or otherwise relieved to permit a clamp or leg lock 136 associated with each leg 120 to lock the first leg element relative to the second leg element once the desired leg length is set. That is to say, the leg lock 136 may lock its respective leg 120 at any one of a plurality of lengths. In one embodiment, the leg lock 136 is formed by a simple camming lock lever 138 that is movable between a first or loosened position (not shown), wherein the two leg elements may move (telescope) relative to one another, and a second or locked position (shown), wherein the leg lock applies a compressive load to squeeze the second leg element 134 against the first leg element 132 and prevent any such relative movement.

In addition to the frame member 110 and the three legs 120, the system 100 may also include a truncated, ball or spherical member 140 adapted to be received within the socket 128 such that the spherical member may rotate about a center of rotation 160 (see, e.g., FIG. 4) defined by the socket. In some embodiments, the spherical member 140 includes an inner surface 155 defining a bore 151 (see, e.g., FIG. 3) passing through the spherical member. The bore 151 may, as stated above, receive other components (e.g., a center positioner 150) that assist with the configuration of the system and/or the implantation of the medical device 102.

The system 100 may further include a lock member 142 (see also FIG. 2) associated with one or both of the socket 128 and the spherical member 140. In one embodiment, the lock member 142 may include two strip-like spherical elements 144 that are connected to one another at one end with a hinge (not shown), and at the other end with a camming lock lever 146. In another embodiment (see, e.g., FIG. 1), the lock member 142 may include a single strip-like, flexible (e.g., metal such as stainless steel) member that mimics the localized shape of the spherical member 140. Like the camming lock lever 138, the lock member 142 (e.g., lock lever 146) may be movable between a first or loosened position (broken lines in FIG. 2), wherein the lock member 142 allows the spherical member to freely rotate within the socket; and a second or locked position (solid lines in FIG. 2), wherein the lock member immobilizes the spherical member relative to the socket, e.g., by squeezing the socket segments 122 against the spherical member 140.

As used herein, the term "spherical guide assembly" or "ball guide assembly," which is identified by reference numeral 141, may refer to the combined assembly of the three independent socket segments 122 (that together define the socket 128), the spherical member 140, and the lock member 142. Any components received within the bore 151 (FIG. 3) of the spherical member 140 (e.g., the center positioner 150) may also form part of the assembly 141. For simplicity of description, the first, second, and third legs may be understood as connecting both to the spherical guide assembly 141 and to the frame member 110.

The construction of the spherical guide assembly 141 may thus restrain the spherical member 140 from all but rotation within the socket 128, effectively allowing almost infinite adjustment in the alignment or trajectory of the bore 151 (and thus of the medical device 102). When combined with the adjustable length legs 120, the system 100 may also accommodate most any device entry point (e.g., burr hole 104) location. Moreover, once leg length and spherical member rotation have been set, both the legs and the spherical member may be locked in place, yielding a surgical fixture now customized for the intended patient. Still further, as described below, such configuration may be performed pre-operatively, after which the system 100 may be moved into the surgical environment, attached to the patient, and the surgical implantation performed without additional system adjustment. However, if needed, intra-operative adjustment may be accommodated.

Figure 2:
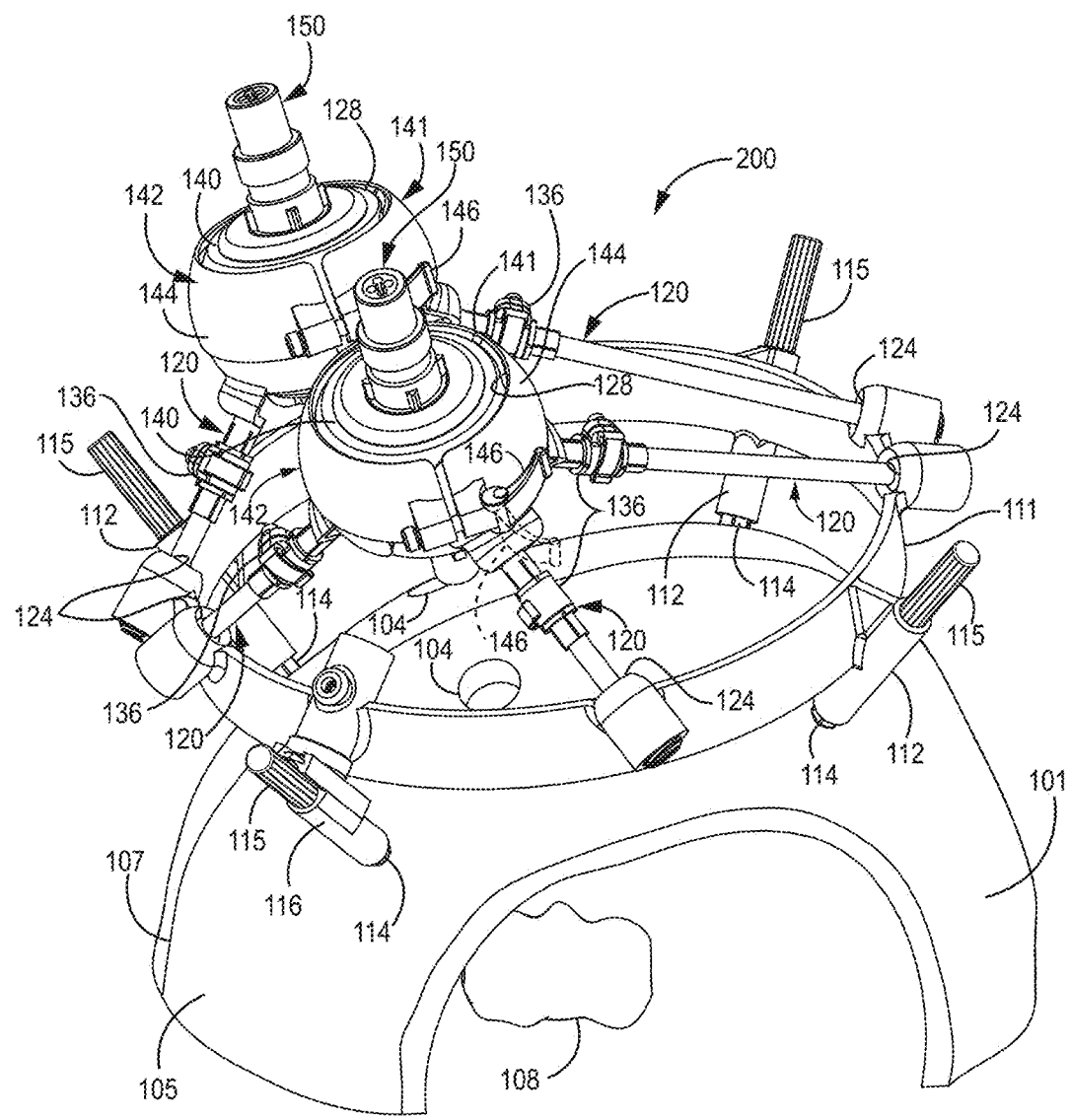
FIG. 2 is a perspective view of a bilateral implantation system (e.g., having dual spherical guide assemblies) in accordance with another embodiment of the disclosure, the system adapted to position two elongate medical devices in three-dimensional (e.g., intra-cranial) space.

As shown in FIG. 1, the system 100 may include the frame member 110 having three leg sockets 124 to receive the three legs 120. Such a configuration may provide for unilateral (e.g., single) device implantation. However, such a configuration is not limiting as systems for implanting multiple devices are also contemplated. For example, a bilateral implantation system 200 is shown in FIG. 2. Such a bilateral system may allow for the implantation of two leads or catheters in the same or, as illustrated, separate burr holes 104, e.g., one located on each side of the sagittal plane 107.

The bilateral system 200 may be similar in most respects to the unilateral system 100 described above. For example, it may include a frame member 111 attachable to fiducials 114 on the skull 105 with three anchor points 112/thumb screws 115 (and an optional, supplemental and lockable sliding anchor point 116 also attached to a corresponding skull-attached fiducial 114). Moreover, the system 200 may also include not one but two (e.g., first and second) spherical guide assemblies 141 (each incorporating a socket and a spherical member) that are each constructed in a manner generally identical to the spherical guide assembly 141 already described above with reference to FIG. 1.

To accommodate the two spherical guide assemblies 141, the system 200 of FIG. 2 requires a frame member 111 that differs from the frame member 110 in that it includes accommodations for an additional three (e.g., fourth, fifth, and sixth) legs 120. That is, the frame member 111 includes six leg sockets 124 (only five visible in FIG. 2) instead of the three sockets provided with the frame member 110 (such a construction allows the two spherical guide assemblies 141 to be positioned independently of one another). The fourth, fifth, and sixth legs 120 may again be of adjustable length. Moreover, in the system 200, the legs 120 may be of differing length ranges (see, e.g., two longer legs toward right side in FIG. 2) to accommodate the desired range of positioning of the bilateral spherical guide assemblies 141. Of course, in other embodiments, the legs 120 of the system 200 could, like the legs of the system 100, be generally identical. Similarly, one or more of the legs of the system 100 could be of a different length range than the others to again provide greater flexibility in positioning the spherical guide assembly. In fact, either or both of the systems 100 and 200 could include multiple legs, or multiple sets of legs, of the same or varying length ranges to accommodate most any spherical guide assembly positioning.

Figure 3:
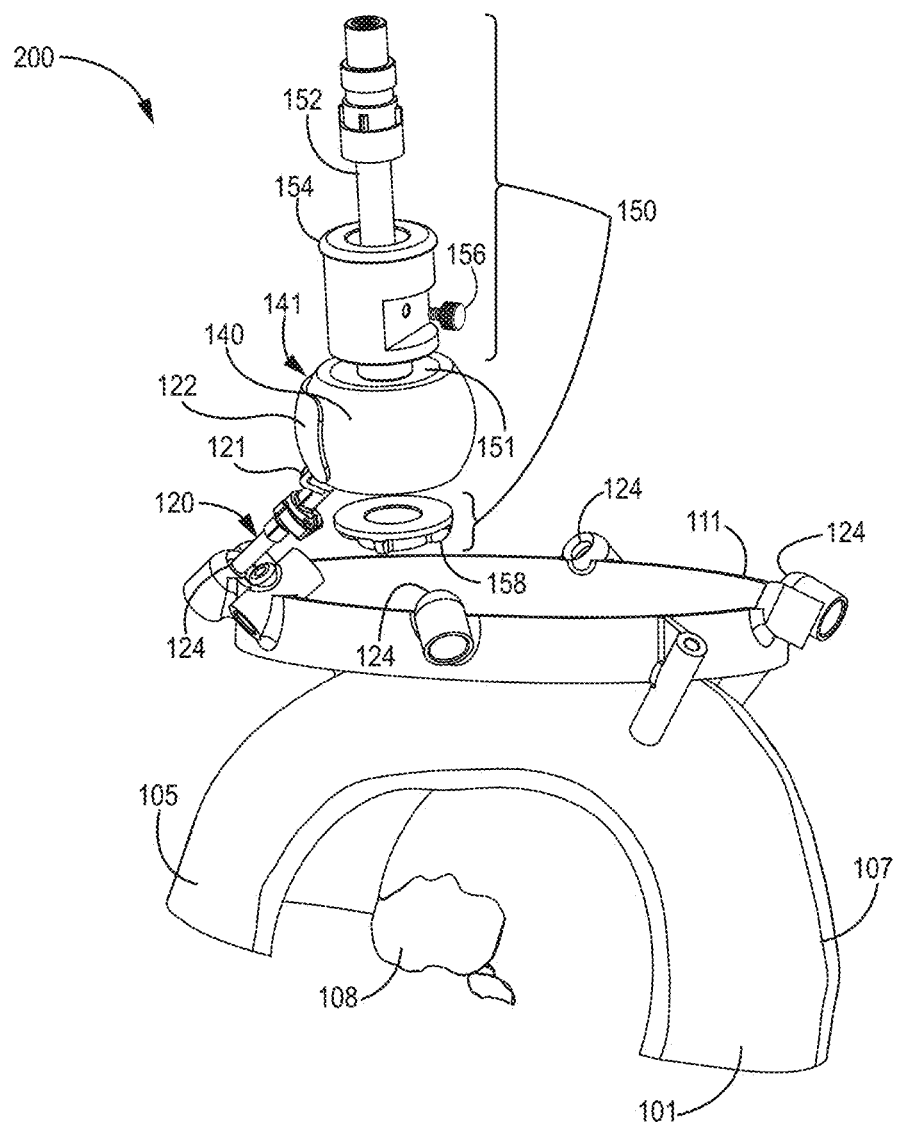
FIG. 3 is a partial exploded view of a single spherical guide assembly of the bilateral system of FIG. 2 (or, alternatively, of the unilateral system of FIG. 1)
Figure 4:
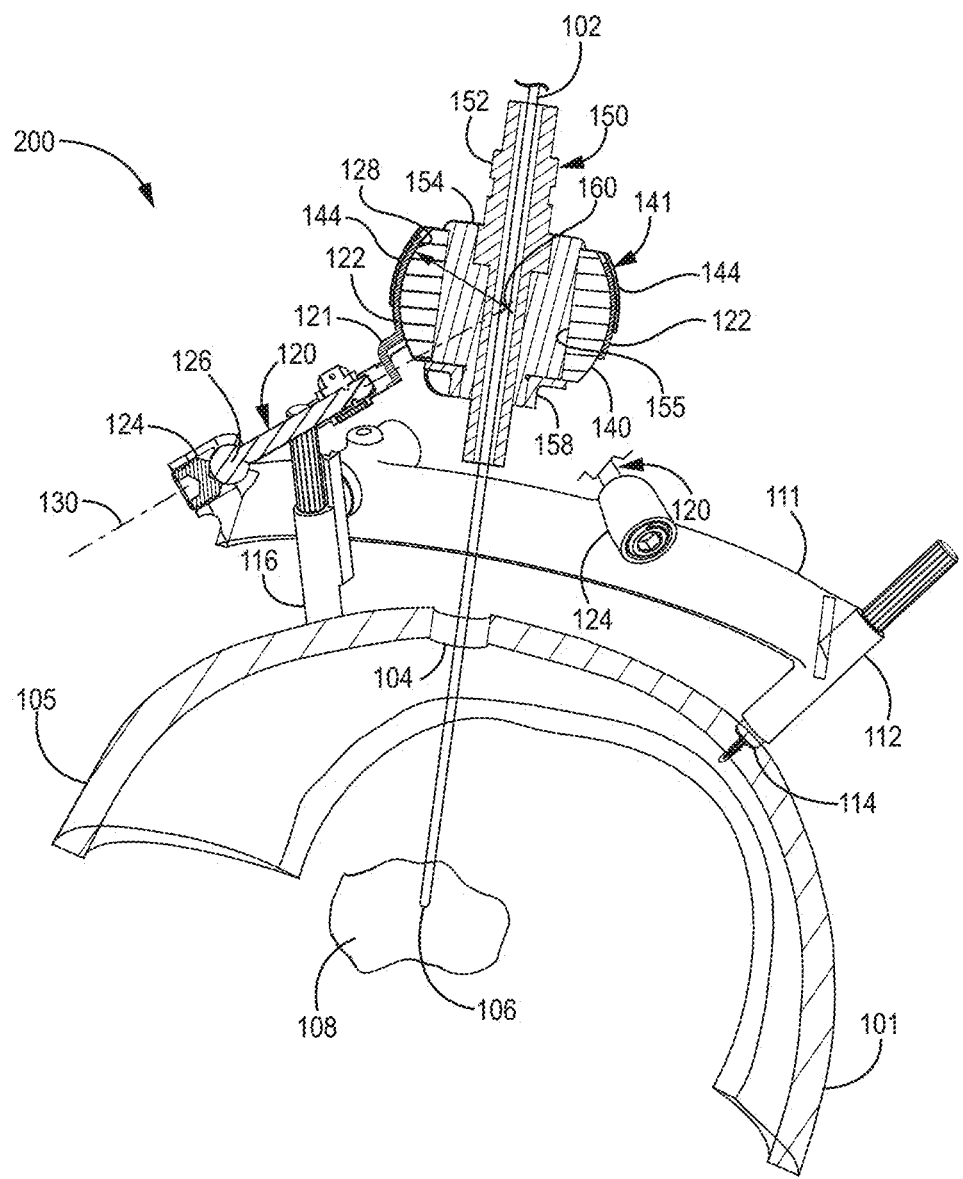
FIG. 4 is a section view taken through one of the spherical guide assemblies of FIG. 2 (or FIG. 1) with some structure removed.
Figure 5:
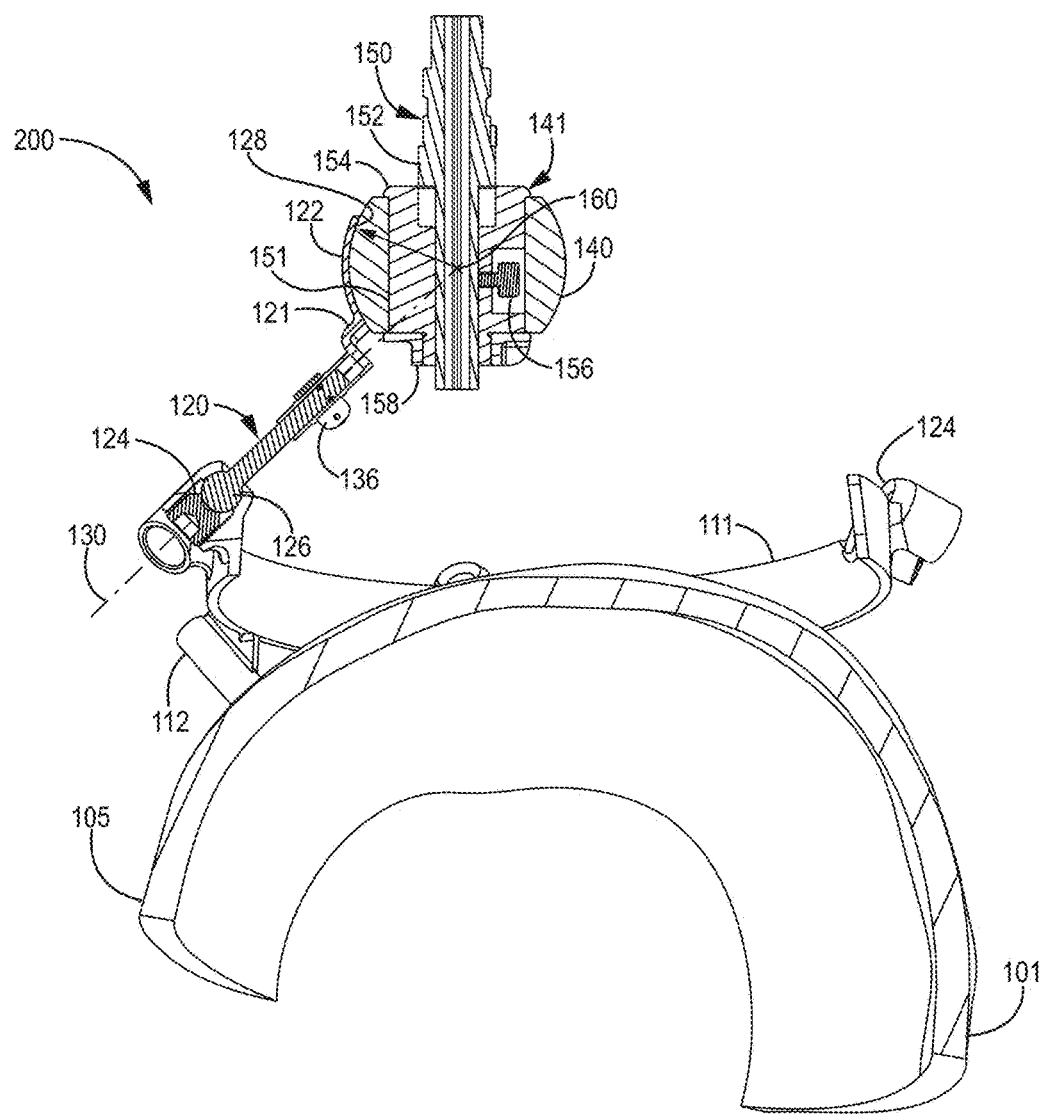
FIG. 5 is another section view taken through one of the spherical guide assemblies of FIG. 2 (or FIG. 1) with some structure removed.

FIG. 3 is a partial perspective view of the system 200 with some structure (e.g., one spherical guide assembly 141 and all but one leg 120) removed and with other structure shown exploded, while FIGS. 4-5 illustrate two different partial section views of one leg 120 and one spherical guide assembly 141 of the system 200. As shown in these views, each of the spherical guide assemblies 141 (whether in the unilateral system 100 or the bilateral system 200) may include the three socket segments 122 (e.g., one formed by the first end 121 of each leg 120 (only one leg shown in FIGS. 3-5)), and the spherical member 140. The spherical member 140 may rotate, within the socket 128 defined by the socket segments 122, about a center of rotation 160 (see, e.g., FIGS. 4 and 5).

An exemplary center positioner 150 may be located within the bore 151 of the spherical member 140 as indicated. In one embodiment, the center positioner includes an alignment sleeve 152 secured to an adapter 154 by a lock screw 156. The adapter 154 is then received in the bore 151, where it is secured in place by a retention nut 158. The center positioner 150 may, among other functions, be used to hold and guide the medical device during implantation.

Figure 6:
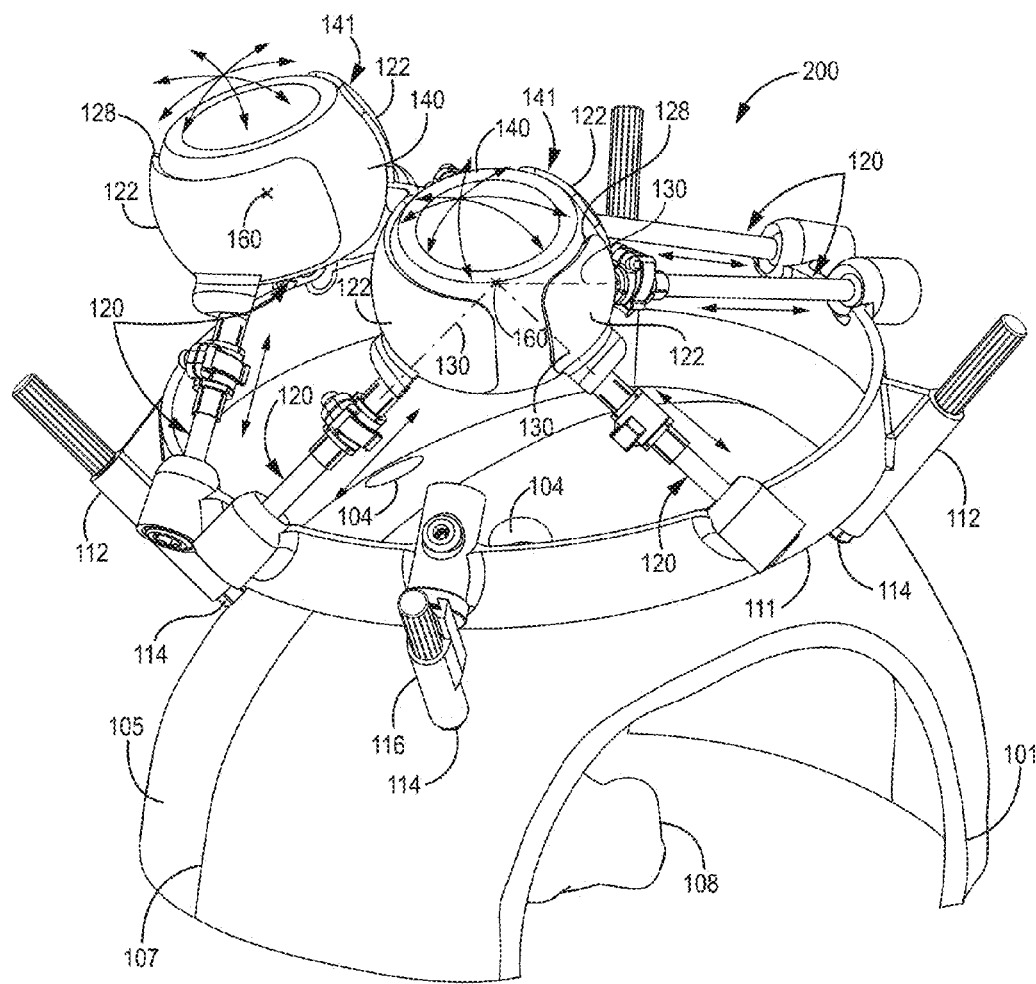
FIG. 6 is a perspective view of the system of FIG. 2 with some structure (e.g., device center positioners, and lock members) removed from the spherical guide assemblies.

As shown in FIGS. 4, 5, and 6 the longitudinal axis 130 of each of the three legs 120 (of each spherical guide assembly 141) may form a tetrahedron, with all longitudinal axes 130 (of the legs of each spherical guide assembly) intersecting at the center of rotation 160 of the socket, regardless of the length setting of the legs. Again, the length of each of the three legs 120 associated with each spherical guide assembly 141 may be adjusted as indicated by the directional arrows in FIG. 6. Moreover, the spherical member 140 of each of the spherical guide assemblies 141 may infinitely rotate within the socket 128 defined by the associated socket segments 122. As the spherical guide assembly generally forms a ball-and-socket device, the spherical member 140 may rotate in any direction about the center of rotation 160 defined by the socket 128 (assuming the lock member 142 (not shown in FIG. 6, but see FIG. 2) is in the unlocked position) as represented by the rotational direction arrows in FIG. 6. As a result, the desired body entry point and device trajectory may be achieved by extension/retraction of the legs 120, and rotation of the spherical member 140.

Figure 7:
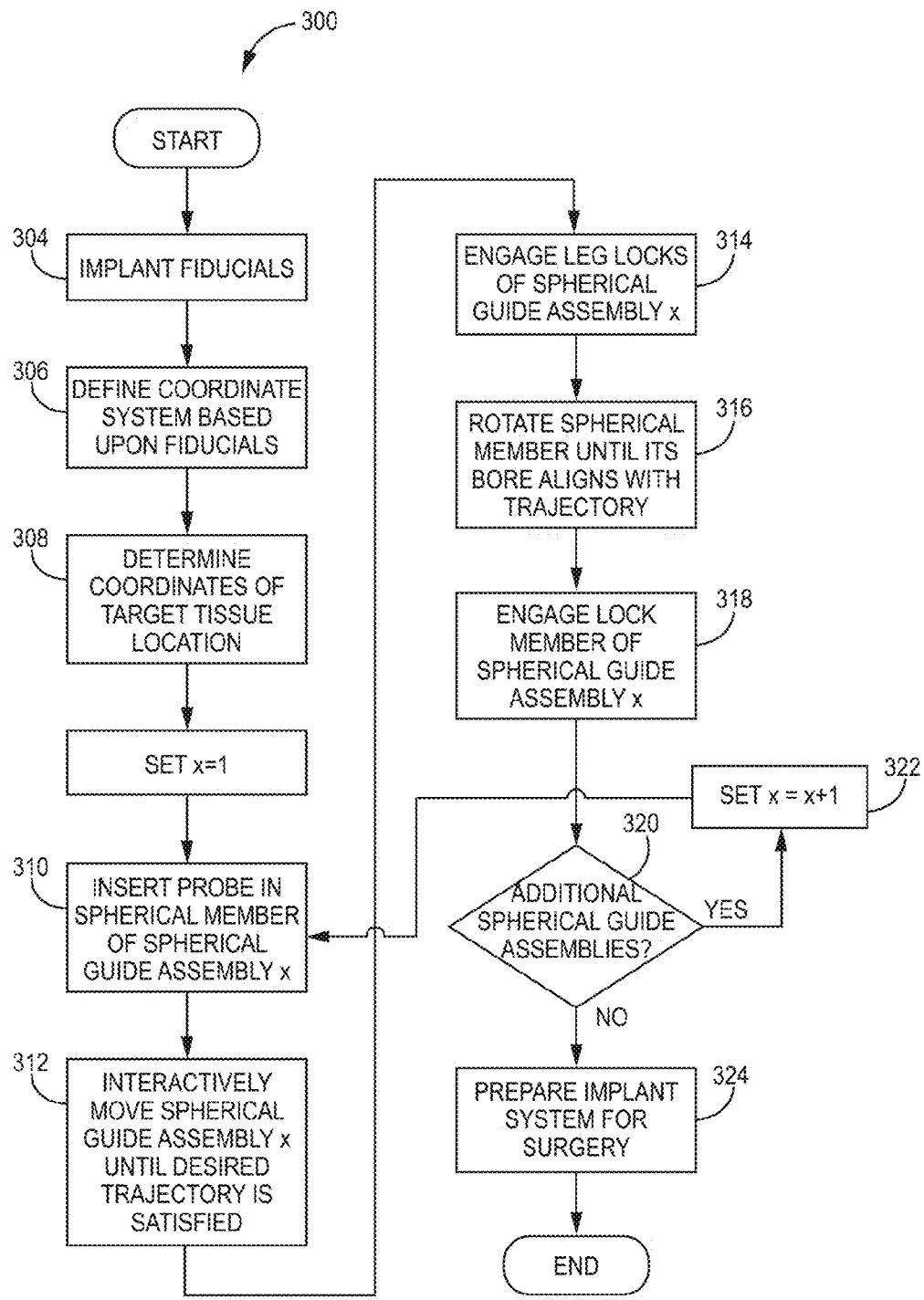
FIG. 7 is a flow chart illustrating an exemplary implantation procedure using an implantation system in accordance with one or more embodiments of the present disclosure.

With FIGS. 1-6 illustrating various implantation systems in accordance with embodiments of the present disclosure, FIG. 7 provides a flow chart illustrating an exemplary process or method 300 for configuring such an implantation system.

Figure 8:
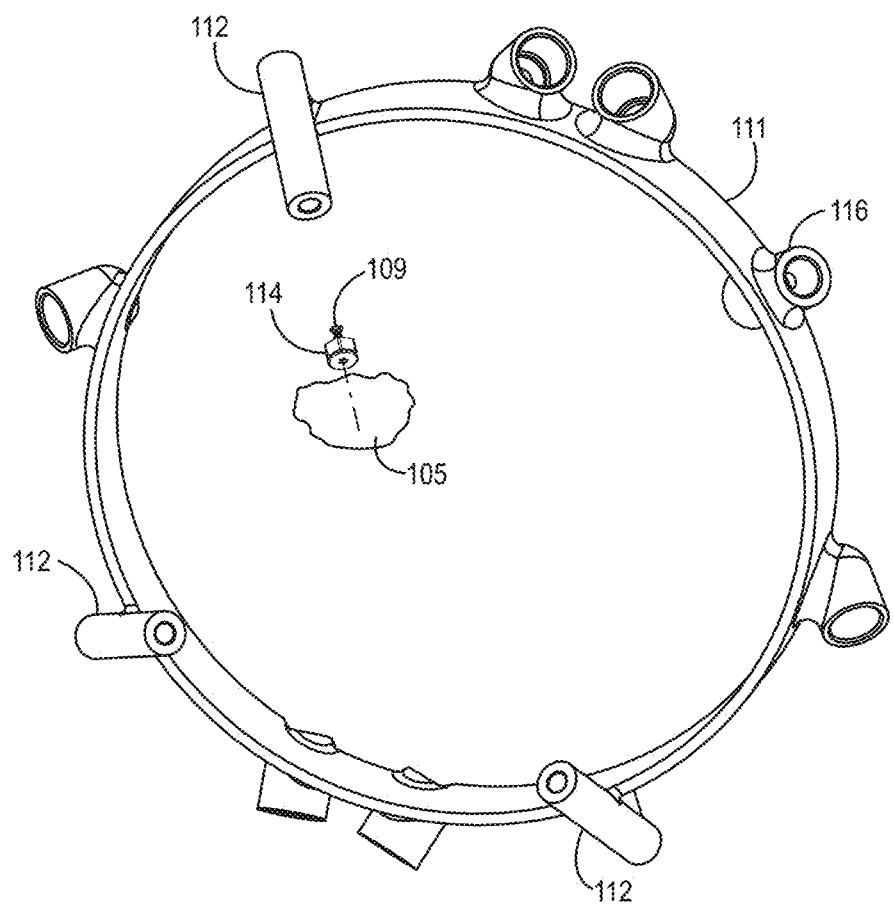
FIG. 8 is a perspective view of the frame member for the bilateral system of FIG. 2, the frame member shown prior to attachment to a body (e.g., skull) surface.

Initially, reference points (e.g., fiducials 114) are implanted or otherwise attached to the patient's body 101 (e.g., skull surface) as indicated at 304. In some embodiments, the frame member 111 (or 110) may be used as a template to establish the locations of the fiducials 114. Each fiducial 114 may then be attached to the skull 105 with a bone screw 109 (after first exposing the skull) as indicated in the perspective view of FIG. 8 (only one fiducial/bone screw shown, but system 200 (and system 100) may use four such fiducials as described above).

With the fiducials 114 implanted, the frame member may be removed from the patient. The patient may then undergo computed tomography (CT) scans to identify the precise position of each reference point (e.g., each fiducial) and establish a common coordinate system based thereon at 306. Magnetic resonance imaging (MRI) may also be performed to identify or otherwise determine coordinates of the target tissue location(s) 108 (see FIG. 2) at 308, i.e., coordinates of the desired implant location of the therapy delivery tip 106 of the device(s) 102 (see FIG. 4). These two datasets may then be merged, e.g., using surgical planning software, to produce a common coordinate system containing both the fiducials and the target tissue location(s).

Figures 9A, 9B:
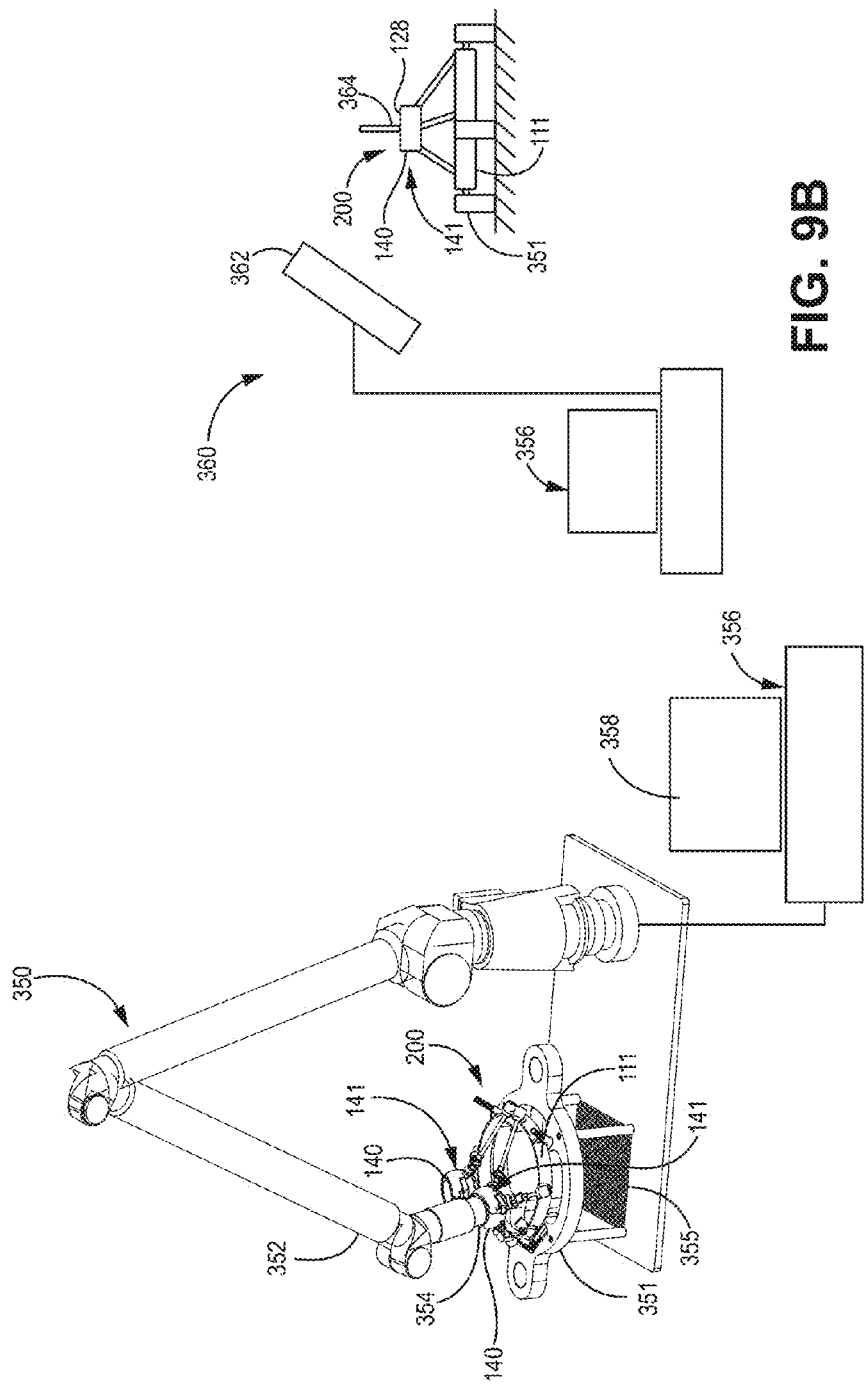

The frame member 111 may then be secured in a fixture that will be used to align and configure the system 200 (or system 100) prior to surgery. While different methods may be utilized, the system may, in some embodiments, be aligned with the use of a coordinate measuring machine (CMM) 350 as shown in FIG. 9A. For instance, with the frame 111 immobilized in a fixture 351 located proximate the CMM, an arm 352 (movable in three-dimensional space) of the CMM may be indexed to the first socket 128/spherical guide assembly 141 (e.g., a probe 354 of the arm may be engaged with the bore 151 of the spherical member 140 (see FIG. 3) and secured or indexed relative to the center of rotation 160 (see FIG. 4) of the socket 128) as indicated at 310 in FIG. 7. The probe 354 may be operatively connected to a computer 356 running the surgical planning software (e.g., StealthViz Advanced Visualization Application sold by Medtronic, Surgical Technologies Division of Louisville, Colo., USA) so that real time, interactive feedback of CMM/probe movement may be reflected in the planning software interface (e.g., on a computer screen 358).

With the leg locks 136 and the lock member 142 (see FIG. 2) in their respective loosened positions, the arm 352/spherical guide assembly 141 (e.g., the center of rotation 160) may be moved or positioned within the established coordinate system while interactively observing coordinates of the probe (using position data from the CMM) in the planning software interface in real time at 312. Because the probe 354 of the CMM 350 is indexed to the center of rotation 160 (see, e.g., FIG. 4) of the spherical guide assembly 141, the actual orientation of the spherical member 140 within the socket 128 is irrelevant at this stage. That is, the trajectory of the medical device is dependent on two points: the target tissue location 108 (known by the planning software and displayed on the computer screen 358); and the center of rotation 160 of the socket 128/spherical guide assembly 141 (which is also visible in the planning software as a result of the probe 354).

By moving the CMM arm 352, the spherical guide assembly 141 may be positioned, with feedback from the planning software, until a desirable trajectory is obtained. Once this occurs, the leg locks 136 (see FIG. 2) may be moved to their respective locked positions at 314 (e.g., the leg lock 136 of each leg 120 may be engaged), thereby locking the position of the socket 128 (e.g., locking the location of the center of rotation 160 of the spherical guide assembly 141) in place.

Once the socket 128 is so fixed in space, the CMM arm 352 may again be moved solely to rotate the spherical member 140, within the socket 128, until a centerline of its bore 151 (see FIG. 3) aligns with the just-established trajectory at 316. Once the bore is so aligned, the lock member 142 of the spherical guide assembly 141 may be moved to its locked position at 318, thereby immobilizing or fixing the spherical member relative to the socket. At this time (or following movement of the leg locks 136 at 314), the depth from the center of rotation 160 to the target tissue location 108 may be measured and recorded for subsequent input to a micro-targeting drive (described below).

In the case of the bilateral system 200, items 310, 312, 314, 316, and 318 may be re-executed for the second spherical guide assembly 141 as indicated at 320 and 322. After alignment of the second spherical guide assembly (or after alignment of the first spherical guide assembly for the unilateral system), the process may then move to step 324, wherein the system 200 (or system 100) is removed from the fixture 351 and prepared for introduction into the surgical environment at 324. If desired, a phantom frame could be provided to confirm that the system is correctly configured before proceeding to surgery. Alternatively, a laser (not shown) could be placed in the bore 151 of the spherical member(s). Then, using a grid 355 that corresponds to the coordinate system established by the planning software, system alignment could be pre-operatively validated.

By aligning the system sequentially in this manner, the positioning of the spherical guide assemblies 141 and engagement of the leg locks (see 312 and 314 of FIG. 7) may be considered as a "macro" or "course" adjustment to alignment, while positioning and locking of the spherical member 140 within the socket 128 (see 316 and 318 of FIG. 7) may be considered more as a "micro" or "fine" adjustment.

A CMM-guided alignment system as shown in FIG. 9A may be advantageous as it provides micrometer-level precision. However, other embodiments may utilize different guidance systems to permit configuration of the system 200 (or system 100). For example, as shown in FIG. 9B, an optical system 360 such as the StealthStation S7 Surgical Navigation System sold by Medtronic, Surgical Technologies Division of Louisville, Colo., USA operating on the computer 356 may be used to optically detect the fiducials with a camera 362 and, using a reflective probe 364 (secured relative to the center of rotation 160 of the socket 128) as a surrogate for the medical device 102, configure the system by moving the spherical guide assembly 141 within the coordinate system, and observing the coordinates of the probe 364 in real time using the camera 362. In yet other embodiments, iterative or manual processes could be used to achieve the desired alignment.

Figure 10:
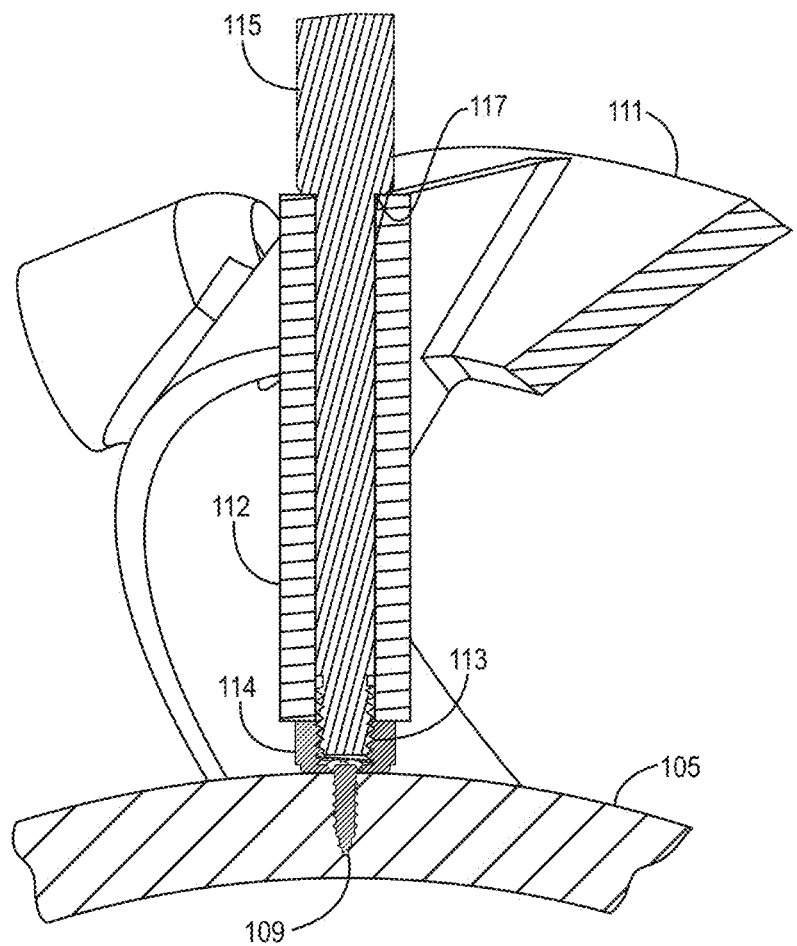
FIG. 10 is an exemplary section view of an anchor point used to secure the frame member to a body (e.g., skull) surface.

During the subsequent surgical procedure, the frame member 111 (or 110) may be attached to the reference points (e.g., to the fiducials 114) as shown in FIG. 10. For example, as shown in this view, each anchor point 112 may be initially set upon its corresponding fiducial 114. Each fiducial 114 may include a female thread 113 adapted to threadably receive a threaded end of the thumb screw 115. A shoulder 117 of the thumb screw 115 may then axially restrain the anchor points 112 and 116, and thus the frame member 111 (or 110), relative to the skull 105.

Figure 11:
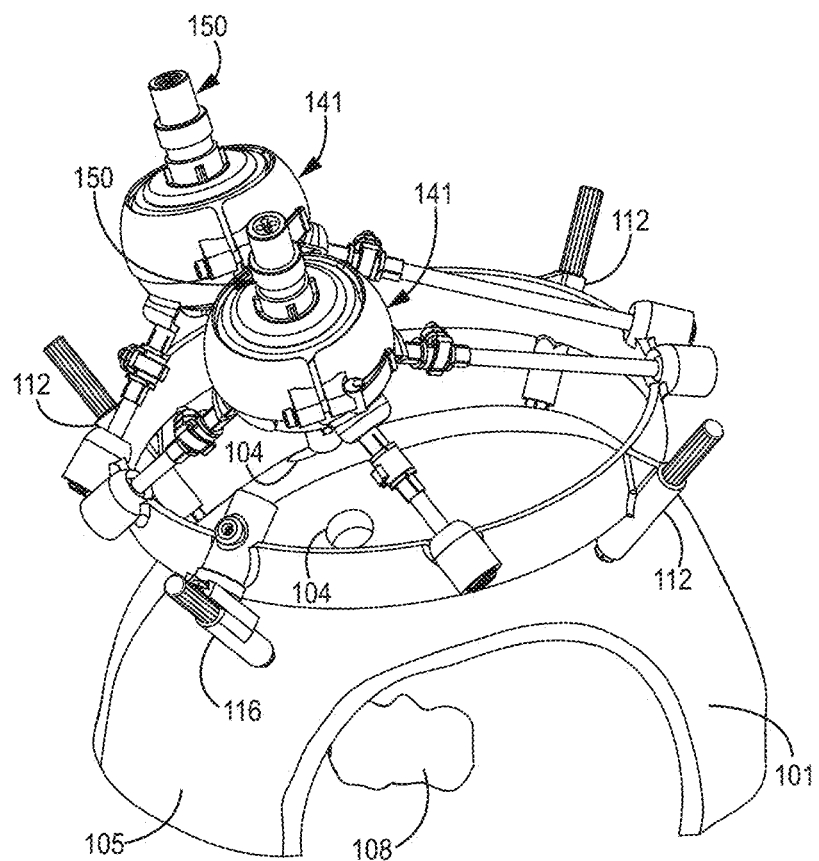
FIG. 11 is a perspective view of an exemplary bilateral system attached to a skull.

Once all four anchor points 112, 116 are tightened to their respective fiducials 114 as shown in FIG. 11, the burr holes 104 may be formed. In one embodiment, the center positioners 150 may be removed and the bore 151 of each of the spherical members 140 used as a pilot to mark the cranial drill points of the respective burr holes (after which a drill may pass with clearance through the spherical members to form the burr holes). Alternatively, the burr holes could be formed prior to attachment of the frame member to the skull 105.

Figure 12:
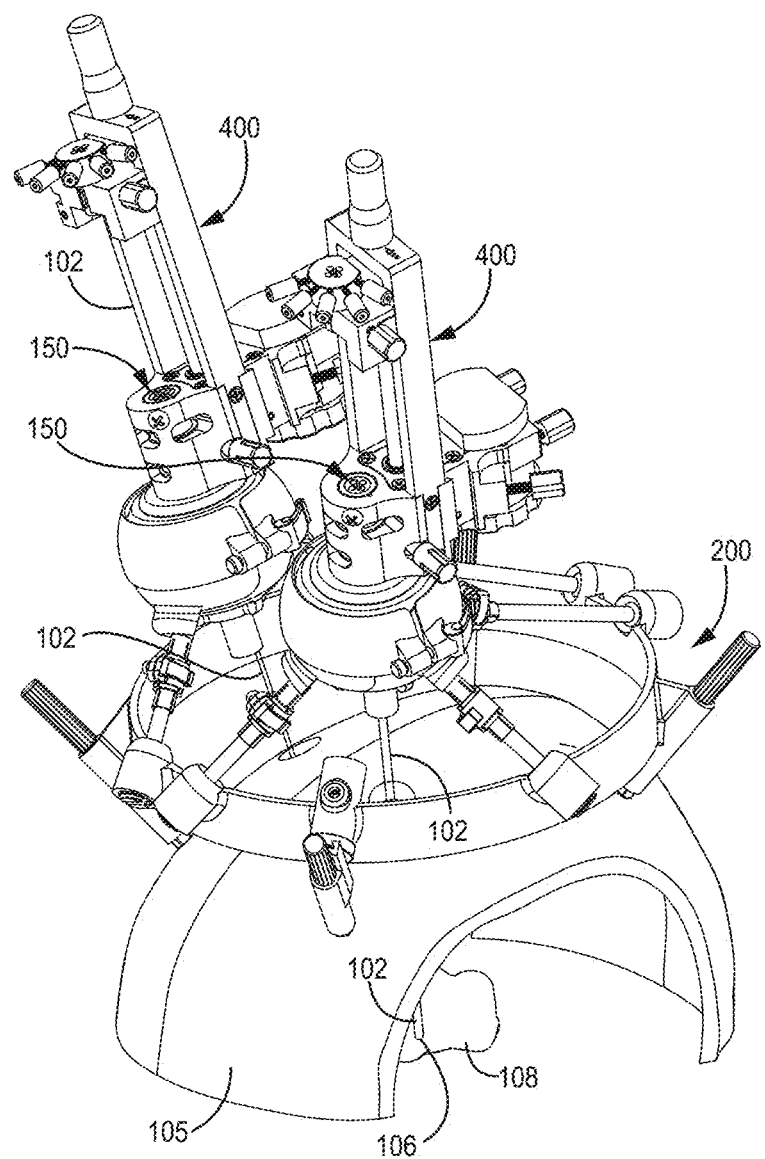
FIG. 12 is a perspective view similar to FIG. 11, but additionally illustrating a cannula and a surgical insertion drive associated with each of the spherical guide assemblies.

Once the burr holes 104 are formed, the center positioners 150 may be reattached and a surgical insertion drive 400 (e.g., a STar Drive micro-targeting drive sold by FHC Inc. of Bowdoin, Me., USA) attached as illustrated in FIG. 12. The drive 400 may be used to implant the medical device(s) 102 and may also, based upon the previously determined depth to target calculations, set the implantation depth that will position each therapy delivery tip 106 of the therapy delivery device (e.g., lead 102) at the desired target tissue location 108. As micro-targeting drives (as well as other surgical insertion drives) are known, further description is not provided herein.

Stereotactic systems, apparatus, and methods in accordance with embodiments of this disclosure may provide a system and procedure that presets therapy delivery device guidance parameters in a pre-operative setting. As a result, time consuming, intra-operative adjustments, as well as potential adjustment errors during surgery, may be reduced or even avoided. Moreover, frame members like those described herein may be lightweight and comfortable for the patient, while still providing precision placement of unilateral or bilateral therapy delivery devices. Still further, although described in the context of brain implantation, systems, apparatus, and methods in accordance with embodiments of the present disclosure may be useful in any application wherein accurate guidance of a lead, catheter, or other elongate medical device is required.

Illustrative embodiments are described and reference has been made to possible variations of the same. These and other variations, combinations, and modifications will be apparent to those skilled in the art, and it should be understood that the claims are not limited to the illustrative embodiments set forth herein.

What is claimed is:

1. An implantation system for positioning an elongate medical device in three-dimensional space, the system comprising:
   a frame member;
   first, second, and third legs each having an adjustable length, wherein each of the first, second, and third legs comprises:
      a first end comprising an integral concave end portion forming a socket segment, wherein a combined assembly of the socket segments of each of the first, second, and third legs together define a socket; and
      a second end connected to the frame member; and
   a spherical member adapted to be received within the socket such that the spherical member may rotate about a center of rotation defined by the socket, the spherical member comprising an inner surface defining a bore passing through the spherical member.

2. The system of claim 1, further comprising a lock member associated with one or both of the socket and the spherical member, the lock member movable between:
   a first position wherein the spherical member is free to rotate within the socket; and
   a second position wherein the spherical member is immobilized relative to the socket.

3. The system of claim 1, wherein each of the first, second, and third legs comprises a leg lock adapted to lock its respective leg at any one of a plurality of lengths.

4. The system of claim 1, wherein the frame member comprises a ring.

5. The system of claim 4, wherein the ring comprises anchor points each adapted to secure the ring to a corresponding reference point on a mammalian body.

6. The system of claim 5, wherein the anchor points comprise three fixed anchor points and one sliding anchor point.

7. The system of claim 4, wherein the ring comprises anchor points each adapted to secure the ring to a corresponding reference point on a human skull.

8. The system of claim 1, wherein each of the first, second, and third legs defines a longitudinal axis and wherein each of the longitudinal axes intersect one another at a point within the socket along the center of rotation defined by the socket regardless of the adjusted length of the first, second, and third legs.

9. The system of claim 8, wherein each of first, second, and third legs is adapted to rotate about its respective longitudinal axis.

10. The system of claim 1, further comprising:
    fourth, fifth, and sixth legs each having an adjustable length, wherein each of the fourth, fifth, and sixth legs comprises:
       a first end comprising a second socket segment, wherein the second socket segments of each of the fourth, fifth, and sixth legs together define a second socket; and
       a second end connected to the frame member; and
    a second spherical member adapted to be received within the second socket such that the second spherical member may rotate about a center of rotation defined by the second socket, the second spherical member comprising an inner surface defining a bore passing through the second spherical member.

11. A system for implanting an elongate medical device into a mammalian skull through a predetermined entry point and at a predetermined trajectory, the system comprising:
    a frame comprising three or more anchor points;
    a spherical guide assembly comprising: three independent socket segments that together define a socket; and a spherical member adapted to be received within the socket such that the spherical member may rotate about a center of rotation defined by the socket, the spherical member comprising an inner surface defining a bore passing through the spherical member; and
    first, second, and third legs, wherein each of the first, second, and third legs has an adjustable length, and wherein each of the first, second, and third legs comprises an integrally formed concave first end portion to define one socket segment of the three socket segments that, when combined together, define the socket, and a second end that is connected to the frame.

12. The system of claim 11, where the anchor points comprise three fixed anchor points and one sliding anchor point.

13. The system of claim 11, wherein end portions of each of the first, second, and third legs attach to the frame via a ball-and-socket connection.

14. The system of claim 11, wherein each of the first, second, and third legs comprises a leg lock adapted to lock the respective leg at any one of a plurality of lengths.

15. The system of claim 11, further comprising an insertion guide adapted to be secured within the bore of the spherical member.

16. The system of claim 11, wherein each of the first, second, and third legs defines a longitudinal axis and wherein each of the longitudinal axes intersect each other at a point within the socket along the center of rotation defined by the socket regardless of the adjusted length of the first, second, and third legs.

17. The system of claim 11, further comprising a lock member associated with the spherical guide assembly, the lock member movable between:
    a first position wherein the spherical member is free to rotate within the socket; and
    a second position wherein the spherical member is immobilized relative to the socket.

* * * * *